United States Patent

Jackson et al.

Patent Number: 5,859,070
Date of Patent: Jan. 12, 1999

[54] CATALYTIC PROCESS

[75] Inventors: Samuel David Jackson, CO Durham; Frederick Ernest Hancock, Cleveland; Bernard John Crewdson, North Yorkshire, all of United Kingdom

[73] Assignee: Imperial Chemical Industries, PLC, London, England

[21] Appl. No.: 624,454

[22] PCT Filed: Oct. 10, 1994

[86] PCT No.: PCT/GB94/02204

§ 371 Date: Jul. 22, 1996

§ 102(e) Date: Jul. 22, 1996

[87] PCT Pub. No.: WO95/11080

PCT Pub. Date: Apr. 27, 1995

[30] Foreign Application Priority Data

Oct. 18, 1993 [GB] United Kingdom .................. 9321470
Apr. 15, 1994 [GB] United Kingdom .................. 9407466

[51] Int. Cl.⁶ ..................................................... C07C 27/00
[52] U.S. Cl. ........................... 518/713; 423/249; 423/376; 423/418.2; 518/700; 518/722; 558/35; 562/847; 568/840; 568/473; 568/474; 570/258
[58] Field of Search ..................... 518/700, 713, 518/722; 568/840; 570/258

[56] References Cited

U.S. PATENT DOCUMENTS

| | | |
|---|---|---|
| 3,499,941 | 3/1970 | Givens et al. . |
| 3,761,579 | 9/1973 | Curtis et al. . |
| 3,769,286 | 10/1973 | Hess . |
| 3,838,070 | 9/1974 | Thomas, Jr. . |
| 3,853,745 | 12/1974 | Welty . |
| 4,547,613 | 10/1985 | Garwood et al. . |
| 4,863,894 | 9/1989 | Chinchen et al. . |
| 5,082,980 | 1/1992 | Berridge . |
| 5,135,722 | 8/1992 | Zardi et al. . |
| 5,137,924 | 8/1992 | Short et al. . |
| 5,217,675 | 6/1993 | Yoshiki et al. . |
| 5,236,878 | 8/1993 | Inoue et al. . |
| 5,278,875 | 1/1994 | Fujisawa et al. . |
| 5,449,696 | 9/1995 | Dandekar et al. . |

FOREIGN PATENT DOCUMENTS

| | | |
|---|---|---|
| 0 089 795 | 9/1983 | European Pat. Off. . |
| 0 109 060 | 5/1984 | European Pat. Off. . |
| 0 332 757 | 9/1989 | European Pat. Off. . |
| 0 462 546 | 12/1991 | European Pat. Off. . |
| 2 180 652 | 11/1973 | France . |
| 109433 | 5/1984 | Germany . |
| 209 433 | 5/1984 | Germany . |
| 2 252 968 | 8/1992 | United Kingdom . |

OTHER PUBLICATIONS

Peng, Journal of Radioanalytical Chemistry: Gas Phase Formation of Methyl and Ethyl Iodides, vol. 65, pp. 61–73 (1981).

Oberdorfer et al., Int. J. Appl. Radiat. Isot., A New Procedure for the Preparation of $^{11}C$ Labelled Methyl Iodide, vol. 36, pp. 435–438 (1985).

Primary Examiner—Michael L. Shippen

[57] ABSTRACT

Synthesis of small quantities of compounds such as methanol from reagents, especially radio-labelled reagents such as $^{11}C$ oxides, in a carrier gas by a catalytic reaction using a catalyst that has been pre-conditioned for the reaction by previous use for the desired reaction and has then been passivated, or has been maintained in the pre-conditioned state, until contacted with said carrier gas. Where the product is adsorbed by the catalyst, it may be desorbed by heating or displaced by contacting the catalyst with a material, e.g. a catalyst poison that is more strongly adsorbed. Such a more strongly adsorbed material may react with the adsorbed catalytic product to produce a desired product.

11 Claims, 2 Drawing Sheets

CATALYTIC PROCESS

This invention relates to catalytic processes and to catalysts therefor.

There is an increasing interest in the production of chemical compounds from very small quantities of a reactant material, especially those containing radio-active isotopes of certain elements.

Thus various techniques can be employed to produce small quantities of primary reagents containing an element isotope having a relatively short half-life. Provided such primary reagents can be converted into a suitable compounds within a relatively short time so that the compound exhibits the desired radioactivity, such compounds can be used as tracers in medical applications, particularly diagnostic medical applications.

An example of a diagnostic technique employing short-lived radio-isotopes in tracer compounds is positron emission tomography (PET). In this technique a target is bombarded with protons, e.g. in a cyclotron, giving rise to radioisotopes. The isotope reacts to produce a radio-labelled primary reagent. For example $^{11}C$ is produced by proton bombardment of a nitrogen target: the $^{11}C$ then reacts with traces of oxygen present to give $^{11}CO_2$ as a primary reagent. Since the half-life of $^{11}C$ is of the order of 20 minutes, it is necessary that the conversion of the $^{11}CO_2$ to the desired tracer is accomplished rapidly. The amount of $^{11}CO_2$ produced is very small, typically less than 1 nanomole per liter (at STP) of the target.

Another $^{11}C$ primary reagent that can be produced is $^{11}CH_4$ (using a mixture of hydrogen and nitrogen as the target). Other radio-labelled isotopes that can be obtained by analogous methods include $^{13}N$, $^{15}O$, and $^{18}F$, and these likewise can be used to introduce the appropriate radio-label into a tracer compound. Thus other primary reagents such as $^{13}NO_2^-$, $^{13}NO_3^-$ and $^{13}NH_4^+$ can be produced by proton bombardment of water as a target; primary reagents such as $^{15}O_2$ can be made by deuteron bombardment of nitrogen, $C^{15}O_2$ can be made by deuteron bombardment of nitrogen containing a small amount, e.g. 2–2.5% v/v, of carbon dioxide; and $^{18}F_2$ from a neon target and $^{18}F^-$ from a $^{18}O$-enriched water target.

Heretofore the primary reagents have been converted into the desired compounds by conventional small scale chemical reaction techniques, often involving a number of separate reaction stages: for example with the primary reagent $^{11}CO_2$, the $^{11}CO_2$, possibly after a preliminary step of adsorbing the carbon dioxide on a molecular sieve from which it is subsequently desorbed by heating, may be reacted with lithium aluminium hydride to form $^{11}CH_3OH$ which is then reacted with aqueous hydrogen iodide, or with diphosphorus tetraiodide, to give $^{11}CH_3I$ which is then used as an alkylating agent to give a tracer compound having $^{11}C$-containing methyl groups. The conversion of the primary reagents to reactive intermediate reagents is often troublesome and gives inconsistent yields. Furthermore although attempts have been made to automate such techniques, a skilled radio chemist is often required.

Even with those primary reagents, e.g. $^{15}O_2$, which can be used directly as tracer materials, purification is often necessary before such use, and presents problems.

It would be desirable to employ simple, automated, catalytic techniques to effect the conversion of many of the desired primary reagents into more reactive intermediate reagents, or to effect reactions of undesired contaminants so as to render purification more facile. However we have found that, largely because of the small amounts of the reagents, conventional catalytic methods present problems. In many cases there is an unacceptable delay between contacting the reagent with the catalyst and appearance of the desired product (by which term we include intermediates which are subsequently converted into other compounds) in the effluent from the catalyst.

We have found that this problem can be overcome by employing a pre-conditioned catalyst.

Accordingly the present invention provides a catalytic process for the reaction of a primary reagent, or contaminants in such a primary reagent, comprising contacting a carrier gas containing the reagent in a very small proportion, together with such other reagent or reagents as may be needed for the reaction, with a catalyst for the desired reaction under reaction conditions favourable to said reaction, wherein the catalyst has been pre-conditioned by previous use for the desired reaction and has been passivated, or has been maintained in the preconditioned state, until contacted with said carrier gas.

It is generally not necessary that the pre-conditioning is effected using the radio-labelled reagent. Thus the pre-conditioning may be effected using unlabeled reagents and then the catalyst passivated, or maintained in the pre-conditioned state, until required for the desired reaction.

The catalyst and the conditions used for preconditioning (and passivation, if employed) will of course depend on the nature of the desired reaction.

For example the production of $^{11}CH_3OH$ from $^{11}CO_2$ may be effected using a copper catalyst at 150°–250° C. at a pressure in the range 20–60 bar abs.

The production of $^{11}CH_4$ from $^{11}CO_2$ may be effected using a nickel catalyst at 200°–300° C. using hydrogen as a reducing agent. The production of $H^{11}CN$ from $^{11}CH_4$ (produced from $^{11}CO_2$ as above or directly by proton bombardment of a nitrogen/hydrogen target) may be effected by reaction of the $^{11}CH_4$ with ammonia in hydrogen at a high temperature, e.g. 800°–1100° C., using a platinum or platinum/rhodium catalyst.

$^{11}CO$ may be made by subjecting $^{11}CO_2$ to the reverse shift reaction using a copper catalyst; $^{11}COCl_2$ may be made from $^{11}CO$ by reaction with chlorine over activated carbon at e.g. 200°–300° C.

$H^{11}CHO$ may be made from $^{11}CH_3OH$ (produced as above) using a silver or iron/molybdenum catalyst and nitrogen or helium as a carrier gas.

$^{11}CH_3I$ may be made by reacting $^{11}CH_3OH$ with a suitable source of hydrogen iodide. Likewise $CF_3$—O—$SO_3^{11}CH_3$ (methyl triflate) may be made by reacting $^{11}CH_3OH$ with silver triflate.

Other $^{11}C$ compounds, such as $R^{11}CH_2I$, $R^{11}COCl$, $(CH_3)_2^{11}CO$ and $(CH_3)_2^{11}CHI$, where R is an alkyl radical, may be made by analogous methods.

$^{15}O_2$ as produced by deuteron bombardment of $^{14}N_2$ or by proton bombardment of $^{15}N_2$ is liable to be contaminated by labelled compounds such as carbon and nitrogen oxides and ozone. Separation of $^{15}O_2$ from such contaminants may be effected using pre-conditioned absorbents such as alkalised alumina, or suitable metals or metal oxides.

$H_2^{15}O$ may be made by reaction of $^{15}O_2$ produced as above with hydrogen over a catalyst such as supported platinum, palladium, or, particularly, rhodium, at ambient or higher temperatures, e.g. 150°–200° C. In order to minimise adsorption of the product $H_2^{15}O$ on the catalyst support, the support is preferably alpha-alumina, quartz, or a non-oxidic material such as a boride, e.g. tantalum boride, or a carbide such as silicon carbide.

In many cases it is found that while the desired product is produced, it may be adsorbed on the catalyst. Desorption of the adsorbed product may be effected by heating in a carrier gas stream and/or the adsorbed product may be desorbed or displaced from the catalyst by contacting the catalyst, having the product adsorbed thereon, with a carrier gas stream containing a reagent that is more strongly adsorbed by the catalyst than the desired product. A suitable reagent to effect desorption is often a compound that acts as a poison for the catalytic reaction involving the reagent. The nature of the poison will of course depend on the nature of the catalyst. In some cases the reagent used to effect poisoning of the catalyst and desorption of the product, may be a reagent that causes a further desired reaction of the product. For example, where a copper catalyst is used for the synthesis of $^{11}CH_3OH$, the $^{11}CH_3OH$ generally remains adsorbed on the catalyst. By contacting the catalyst with HI, which serves to poison the catalyst, the $^{11}CH_3OH$ desorbs and at the same time reacts with the HI to produce $^{11}CH_3I$.

Where the desorption and/or further reaction is effected using a catalyst poison, the catalyst is thus generally usable only once to produce the desired product. Consequently it is preferred to provide the catalyst, in the pre-conditioned state, in a cartridge that can be discarded after use.

Therefore according to a further aspect of the invention, there is provided a sealed cartridge for use in a catalytic process for the reaction of a small amount of a primary reagent, or of contaminants in such a primary reagent, said cartridge containing a quantity of a catalyst for the process and which has been pre-conditioned by using the catalyst for the desired reaction and has then been passivated, or maintained in the pre-conditioned state, and has been sealed under an inert atmosphere to maintain the catalyst in the passivated or pre-conditioned state.

The invention is particularly described with reference to the production of $^{11}CH_3OH$ and the subsequent conversion thereof into $^{11}CH_3I$.

In this process, $^{11}C$ is produced by the proton bombardment of nitrogen: the $^{11}C$ so produced reacts with oxygen to give $^{11}CO_2$, possibly with some $^{11}CO$. The oxygen may be traces which inevitably occur in even well purified nitrogen: alternatively small amounts of oxygen may be added to the nitrogen. Typically the resultant $^{11}CO_2$ containing nitrogen contains only a very small amount of $^{11}C$ carbon oxides, typically less than about 1 nanomole per liter (at STP). The nitrogen may also contain small amounts of $^{12}CO_2$ resulting from traces thereof in the nitrogen or adsorbed on the equipment. The amount of $^{12}CO_2$ is likely to be many times the amount of $^{11}C$ oxides present, and indeed the total carbon oxides content of the nitrogen is typically of the order of 1 $\mu$mole per liter (at STP). Typically the volume of nitrogen employed (expressed at STP) is 0.5 to 5 liters.

The carbon oxides, in a carrier gas, are contacted with a heated methanol synthesis catalyst where reaction with hydrogen takes place to form methanol. The carrier gas may be hydrogen, or an inert gas such as nitrogen or helium containing hydrogen. Alternatively, as described below, hydrogen may be pre-absorbed on the catalyst, in which case the carrier gas may be a hydrogen-free inert gas.

Any methanol synthesis catalyst that is active under the process conditions employed may be used, but since it is generally desirable to effect the methanol synthesis at relatively low temperatures, e.g. below 250° C., particularly 150°–220° C., and at low pressures, below 100 bar abs, particularly 20–60 bar abs. catalysts containing copper, and/or a precious metal such as palladium or rhodium, as the active component are preferred. Copper is preferred as the active component since palladium exhibits some methanation activity, thus giving rise to a possible loss of $^{11}C$ as $^{11}CH_4$, while rhodium is less selective than copper and is liable to give rise to some higher alcohols such as ethanol. Examples of suitable catalysts include copper and optionally one or more oxidic stabilising and/or support materials such as silica, zinc oxide, magnesia, chromia, and alumina. As is described hereinafter, desorption of the synthesised methanol from the catalyst may be difficult: for this reason it is preferred that the amount of stabilising oxides that adsorb methanol is minimised. For this reason it is preferred that the catalyst is free from alumina or chromia. Particularly preferred catalysts are copper or copper/zinc oxide compositions with the copper is a finely divided form. Such catalysts may be made by precipitation of the components as oxides, hydroxides, carbonates, or basic carbonates; preferably the compounds are precipitated as oxides or hydroxides to avoid the introduction of $^{12}C$ compounds into the catalyst. Particularly preferred catalysts are made by precipitation of copper hydroxide followed by a reduction step or co-precipitation of copper and zinc hydroxides followed by calcination and reduction steps. Alternatively the catalyst may be made by impregnation of a suitable support material with a solution of salts of the active components, and possibly of stabilising components as aforesaid, followed by reduction to convert the precipitated or impregnated active component to the metallic state. There may be a preliminary step of calcination to convert the precipitated or impregnated active component, and possibly also any stabilising component, to the oxidic form prior to reduction. However, as described in EP-A-296734, to obtain copper catalysts of high activity it may be desirable to avoid such a calcination step so that the precipitated or impregnated material is converted to the active catalyst without heating to a temperature above 200° C.

Alternatively there may be employed catalysts derived by careful oxidation of alloys of a rare earth metal and copper and/or a precious metal, for example as described in U.S. Pat. No. 5,137,924, or of copper/thorium alloys. Although the aforesaid copper/rare earth alloy derived catalysts tend to be poisoned by carbon dioxide, in the present process the amount of carbon dioxide is liable to be so small that no such poisoning occurs. As described in aforesaid U.S. Pat. No. 5,137,924, such catalysts may be hydrided: with such hydrided catalysts, no separate source of hydrogen may be required, i.e. the carbon oxides in a hydrogen-free carrier gas may be passed over a hydrided catalyst so that hydrogen released from the catalyst reacts with the carbon oxides. It will be appreciated that it may also be possible to avoid the need for hydrogen as, or in, the carrier gas by incorporating a suitable hydrogen-absorbing metal. such as palladium into a methanol synthesis catalyst prepared by the aforementioned route involving reduction of a composition obtained by precipitation or impregnation. During such a reduction, using a hydrogen-containing gas for reduction hydrogen can be absorbed by such hydrogen-absorbing metal components and be available in the subsequent synthesis step for reaction with the carbon oxides. Alternatively the requisite hydrogen may be supplied from a cartridge containing hydrogen adsorbed on to a suitable material e.g. palladium: the hydrogen may be released from this cartridge into the carrier gas by heating. The hydrogen used should of course be adequately purified to minimise the carbon oxides content thereof. Purification may be effected in known manner, e.g. using palladium membranes.

As indicated above with a freshly reduced catalyst, there may be a considerable delay before synthesis of the methanol occurs such a delay is unacceptable where rapid synthesis is required. This delay can be minimised or avoided, by pre-conditioning the catalyst. Thus by employing the catalyst to manufacture some methanol before it is used to make the desired small quantity of e.g. labelled methanol the synthesis of methanol from the small quantity of carbon oxides can be effected rapidly.

After such pre-conditioning by effecting methanol synthesis, the catalyst may be passivated, e.g. as described in GB 1319622 wherein the catalyst is contacted at low temperatures, with an oxidising gas such as oxygen or air, diluted with an inert gas. It will be appreciated that before use of such passivated catalysts, some re-reduction of the catalyst is necessary. It is therefore preferred that the catalyst is pre-conditioned by methanol synthesis as aforesaid, and then stored and handled without permitting ingress of substantial amounts of an oxygen-containing gas, so that the catalyst remains in the reduced, pre-conditioned, state.

The process for the production of the small quantity of methanol is preferably automated. Conveniently, the carbon oxides, e.g. $^{11}CO_2$, are first adsorbed on to a molecular sieve. The methanol synthesis can be conducted in continuous flow or in a "batch" process. For example, in a continuous flow process, the carrier gas can be passed over the molecular sieve and then, at the desired synthesis temperature and pressure, through a vessel containing the pre-conditioned methanol synthesis catalyst, which, if previously passivated, has been re-reduced; by heating the molecular sieve, the carbon oxides thereon can be desorbed to introduce a pulse of the carbon oxides into the carrier gas. The rate of desorption, and hence the width of the pulse, can be controlled by controlling the desorption temperature. Preferably the rate of desorption is such that the pulse width is up to 3 minutes, particularly in the range 30 seconds to 3 minutes. The pulse of carbon oxides in the carrier gas then passes through the vessel containing the catalyst and methanol is synthesised.

In a "batch" process, the vessel containing the molecular sieve is pressurised with carrier gas, the carbon oxides desorbed by heating, and then connection established between the pressurised carrier gas containing the desorbed carbon oxides and a vessel, at a lower pressure, e.g. evacuated, containing the methanol synthesis catalyst. The carrier gas and desorbed carbon oxides thus pass into the methanol synthesis catalyst vessel, which is maintained at the desired synthesis temperature. If it is desired to operate a subsequent methyl iodide synthesis step in continuous flow, the flow through the methanol synthesis vessel may be continuous.

Where the carrier gas is hydrogen, or contains hydrogen, the rate of flow of the carrier gas is typically such that the hydrogen space velocity is in the range 5–200 l of hydrogen (expressed at STP) per g of catalyst per hour.

The amount of synthesis catalyst required is generally relatively small, usually no more than about 300 mg, and preferably less than 200 mg, and may be in the form of a finely divided powder, or preferably small pellets typically of average dimension 0.1–1.0 mm.

With hydrogen as the carrier gas at a pressure of 50 bar abs., at the concentrations of carbon oxides envisaged, at equilibrium over 85% of the carbon oxides would be converted to methanol at a synthesis temperature of 250° C. and over 99% at a synthesis temperature of 200° C. We have found that using a zinc-free copper catalyst derived from precipitated copper hydroxide, conversions corresponding to a close approach to equilibrium can be obtained using 820 mg or more of the catalyst.

As indicated above, in some cases the synthesised methanol may be adsorbed on to the catalyst and is not easily desorbed. Decreasing the amount of catalyst decreases the amount of methanol that remains adsorbed on the catalyst, but may be insufficient to achieve a close approach to equilibrium. Thus when using 820 mg of the above catalyst at 200° C. and 50 bar abs. pressure, the synthesised methanol remained adsorbed on the catalyst: however, when using 130 mg of the catalyst under the same conditions, although about 20% of the carbon dioxide was not converted to methanol, a significant proportion of the synthesised methanol was desorbed from the catalyst. The amount of catalyst employed may thus be a compromise between the amount necessary to obtain a close approach to equilibrium and the amount such that an acceptable proportion of the synthesised methanol is desorbed.

In order to minimise the amount of synthesised methanol that remains adsorbed on the catalyst, steps may be taken, after synthesis, to effect desorption of the synthesised methanol. Thus the temperature may be increased e.g. from a synthesis temperature of 200°–250° C. to a temperature of the order of 280°–320° C. Preferably desorption is effected by rapidly heating the catalyst bed. Alternatively, or additionally, the synthesised methanol may be displaced from the catalyst by a reagent that is more strongly adsorbed by the catalyst. Such reagents include sulphur compounds such as hydrogen sulphide, carbon disulphide, and carbonyl sulphide; halogen compounds such as hydrogen chloride and hydrogen iodide; phosphines; amines: cyanides; and ammonia. In order to avoid the introduction of $^{12}C$ compounds, it is preferred that any such reagent is not a carbon-containing compound. Displacement of the synthesised methanol may be effected by contacting the catalyst with the displacement reagent at a temperature between ambient and 300° C., preferably between 200° and 300° C. In many cases, such displacement reagents act as poisons for methanol synthesis: consequently, where such a displacement reagent is employed it may be necessary to replace the catalyst before a further methanol synthesis step is carried out. To avoid the necessity of changing the catalyst for each methanol synthesis, it may be possible to employ a significantly longer bed of methanol synthesis catalyst. Thus in a first methanol synthesis, the methanol will be synthesised and adsorbed on the initial portion of the catalyst bed. The methanol is then desorbed from this portion of the bed during a subsequent desorption step by passing a stream of carrier gas over the catalyst and introducing a pulse of displacement reagent into the carrier gas: the pulse should be of sufficient size to displace the methanol from that first portion of the bed, but insufficient to poison the whole length of the catalyst bed. In a subsequent methanol synthesis, methanol will be synthesised in the adjacent downstream, unpoisoned, portion of the bed and can subsequently be desorbed by applying a pulse of displacement reagent which will displace the synthesised methanol and poison this downstream portion of the bed. Thus there may be a series of portions of the catalyst bed that are successively used for methanol synthesis and then poisoned during the subsequent desorption step. However there is a risk that desorbed methanol will be adsorbed on the downstream unpoisoned portions of catalyst: this risk may be minimised by providing the bed of such length that it can be used for no more than three sequences of methanol synthesis followed by displacement/poisoning, and/or by effecting the desorption using a carrier gas flow rate sufficient that the desorbed methanol is rapidly transported past the unpoisoned portions of the bed.

Desorption is preferably effected with hydrogen iodide. The hydrogen iodide may be produced by heating a suitable solid reagent, such as a mixture of an alkali metal iodide and an acid adsorbed on a suitable support, e.g. a mixture of potassium iodide, phosphoric acid adsorbed on a support such as a zeolite, e.g. the hydrogen form of zeolite Y, as further described hereinafter. Another suitable source of hydrogen iodide employs a cartridge containing iodine on a suitable support; by passing a hydrogen-containing gas over the supported iodine while heating to e.g. 150° C., the iodine may be vaporised into the hydrogen stream and then the hydrogen/iodine mixture reacted catalytically by passing the mixture over a suitable catalyst, e.g. supported platinum or rhodium. Alumina or carbon may be employed as a support for such a catalyst. Alternatively it may be preferably to produce the hydrogen iodide by hydrolysis of a suitable metal iodide, e.g. silver iodide. The water required for the hydrolysis may be produced by desorbing water from a suitable adsorbent, e.g. molecular sieve, upstream of the metal iodide: a further molecular sieve may be provided downstream of the metal iodide to adsorb any unreacted water.

For convenience, as indicated above, the methanol synthesis catalyst may provided sealed in a cartridge which can be fitted into the apparatus employed. Particularly where the bed of catalyst can only be used for a limited number of syntheses, e.g. where the bed or portions thereof, are poisoned during desorption of adsorbed methanol, the cartridge may contain a number of separate beds which are switched into use as required. As mentioned above it is necessary that the methanol synthesis catalyst be pre-conditioned. Such pre-conditioning may be done before connecting the cartridge to the apparatus. It is not necessary that the pre-conditioning be effected with $^{11}$C carbon oxides: thus we have found that the cartridge may be used for methanol synthesis using $^{12}$C carbon oxides, cooled, and flushed with an inert oxygen-free gas and so maintained in the reduced state for subsequent methanol synthesis and sealed under such an inert atmosphere. The cartridge is then connected into the apparatus to be employed for the synthesis of the small amount of methanol under conditions which prevent the ingress of any oxygen-containing gas. Surprisingly, despite the use of $^{12}$C carbon oxides for the pre-conditioning methanol synthesis, the amount of residual $^{12}$C compounds remaining in the cartridge is minimal and, when subsequently used for the synthesis of $^{11}$C methanol minimal contamination with $^{12}$C methanol results. The cartridge may be designed such that one or more frangible seals is or are broken upon connection of the cartridge to the methanol synthesis apparatus, or upon establishing connection of a bed of a multi-bed cartridge with the gas supply.

The pre-conditioning may be effected by performing methanol synthesis on the sample of catalyst while in the cartridge, or on methanol synthesis catalyst that is then loaded into the cartridge after passivation or maintained in the reduced, pre-conditioned, state by means of a suitable oxygen-free atmosphere. The synthesis conditions employed for the pre-conditioning are not critical but high synthesis temperatures, i.e. above about 250° C., are preferably avoided to minimise loss of activity of the catalyst. Suitably pre-conditioning is effected by using the catalyst for methanol synthesis for 2–4 hours. When the pre-conditioning has been effected, the catalyst is cooled from the synthesis temperature to ambient temperature: the cooling may be effected under a flow of a hydrogen/carbon oxides synthesis gas, or the flow of synthesis gas may be switched to a flow of inert gas before cooling. Before sealing however, the cartridge should be purged of carbon oxides by means of a through flow of inert gas. Where it is desired to employ a hydrided catalyst, or a catalyst having absorbed hydrogen as aforesaid, the inert gas may in fact be hydrogen, alone or in admixture with a gas free from oxygen or compounds thereof.

It has been found that treatment of the pre-conditioned catalyst with hydrogen free from carbon oxides does not effect reduction of the catalyst back to the state it had prior to pre-conditioning: thus methanol is synthesised as soon as carbon oxides are introduced into the hydrogen. As indicated above, if the pre-conditioned catalyst has been passivated, a step of reduction with a hydrogen stream is necessary before the passivated catalyst can be used to synthesise methanol: in some cases it may be found that if the catalyst is passivated and then re-reduced, some time delay occurs before methanol synthesis takes place, i.e. the benefits of pre-conditioning are at least partially lost. It is therefore preferred not to employ a passivation step, but to maintain the catalyst in the reduced, pre-conditioned, state.

The cartridge should of course be capable of withstanding the pressures and temperatures employed for methanol synthesis. Preferably the cartridge contains the methanol synthesis catalyst disposed as one or more beds each of which is disposed within an elongated bore of diameter below 5 mm, particularly in the range 1–3 mm, and typically of length 1–5 cm. However where the methanol synthesis catalyst is disposed as a bed wherein successive portions are used for synthesis followed by a desorption stage that effects poisoning of that portion, the overall bed length should be proportionately greater. The cartridge may be made of stainless steel and the bore or bores therein containing the catalyst bed may have a non-absorbent inner coating.

The invention is illustrated by reference to the accompanying drawings wherein.

Figure 1:
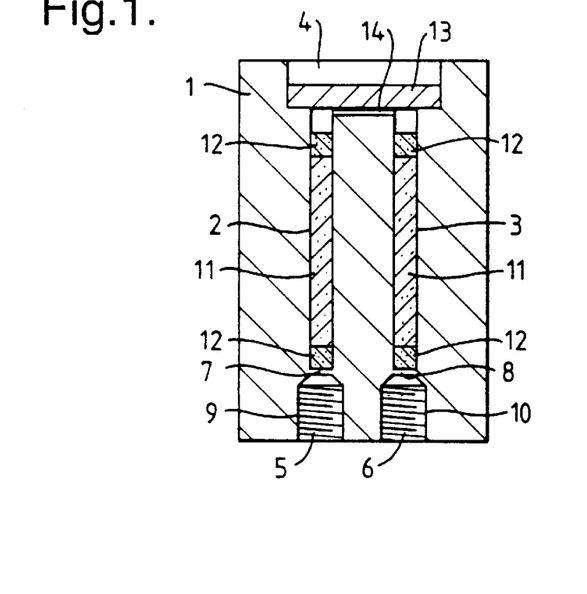
FIGS. 1 and 2 are diagrammatic sections of alternative cartridge designs.

In FIG. 1 there is shown a cartridge in the form of a stainless steel block 1, typically of 35 mm length and 15 mm diameter, having a pair of bores 2, 3 typically of 1–2 mm diameter extending nearly through the block and communicating with a recess 4 in one end of the block 1. At the other end of the block are inlet and outlet ports 5, 6 aligned with bores 2 and 3 respectively but separated therefrom by thin, frangible seals 7, 8. Ports 5, 6 are adapted, e.g. by threaded portions 9, 10, to be connected the apparatus in which the cartridge is to be used. Disposed in each of bores 2, 3 is a bed 11 of a particulate methanol synthesis catalyst with porous retaining plugs 12 at each end of bores 2, 3. After loading the catalyst and porous plugs, the cartridge is sealed by a plug 13 fitted into recess 4. The base of recess 4 is machined to provide a communication path 14 from bore 2 to bore 3.

If, as is preferred, the catalyst is to be reduced and preconditioned before being connected to the methanol synthesis apparatus, the reduced pre-conditioned catalyst should be charged to the bores 2 and 3, and plug 13 applied, while under an inert atmosphere to avoid the ingress of any oxygen containing gas. The methanol synthesis apparatus connections may be arranged to rupture seals 7, 8 as the cartridge is connected to the apparatus.

In some cases it may be desirable that only one of the bores 2, 3 contains methanol synthesis catalyst: where methyl iodide is to be synthesised from the methanol, the inlet bore 2 may contain methanol synthesis catalyst and the outlet bore 3 may contain a suitable solid reagent, for example as described hereinafter, for methyl iodide synthesis.

Figure 2:
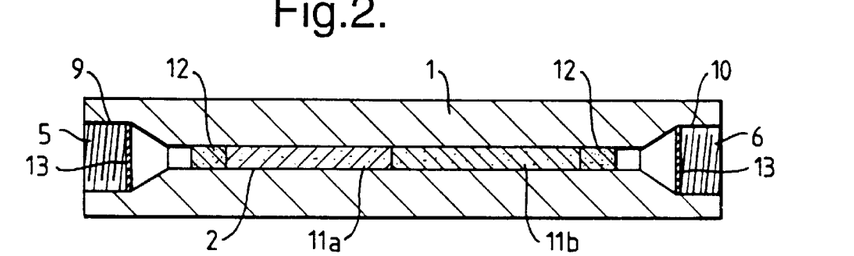

In the cartridge design shown in FIG. 2 there is only a single bore 2 in the block 1, but two catalysts beds 11*a*, 11*b*, or a bed of catalyst 11*a* followed by a bed 11*b* of absorbent or solid reagent, disposed in the bore 2. In this embodiment, thin frangible seal plugs 13 are inserted in the inlet and outlet ports 5, 6 after filling the bore 2. Numerals 9, 10 and 12 have the same significance as in FIG. 1.

Figure 3:
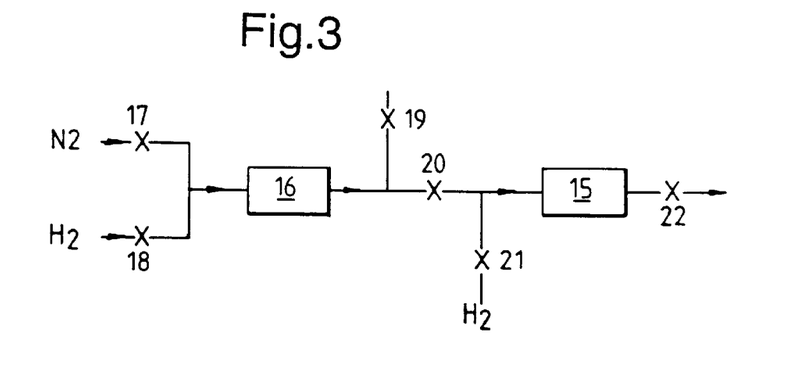
FIGS. 3 to 6 are diagrammatic flow sheets.

Suitable apparatus for the synthesis of the small quantities of methanol is shown in FIG. 3. In this Figure the various valves are shown for simplicity as separate units, but it will be appreciated that they may be combined into suitable multiway, multiport, valve units. The cartridge 15 containing the pre-conditioned methanol synthesis catalyst is connected in series with a cartridge 16 containing a molecular sieve on to which the $^{11}C$ oxides have been adsorbed. Valves 17, 18 are provided to supply nitrogen and hydrogen respectively to the molecular sieve cartridge 16, and valves 19, 20, 21 are provided respectively to purge cartridge 16, to isolate cartridge 16 from cartridge 15, and to supply hydrogen to cartridge 15. A further valve 22 is provided downstream of cartridge 15.

Initially, valves 17, 19, 21, and 22 are open and valves 18 and 20 closed. Cartridge 16 is thus purged with nitrogen, typically at about atmospheric pressure, venting through valve 19, while cartridge 15 is likewise purged at about atmospheric pressure with hydrogen supplied through valve 21 and venting via valve 22. During this purging operation, cartridge 15 is heated to the desired methanol synthesis temperature. Valves 17, 19, 21 and 22 are then closed and valve 18 opened. Hydrogen is thus supplied to cartridge 16 via valve 18 to pressurise cartridge 16 to, for example, 50 bar abs. At the same time cartridge 16 is heated to desorb the carbon oxides into the hydrogen. Valve 20 is then opened and the hydrogen, plus desorbed carbon oxides, flow from cartridge 16 into cartridge 15 via valve 20 thus pressurising the latter. The continued supply of hydrogen via valve 18 ensures that the desorbed carbon oxides are swept from cartridge 16 into cartridge 15. Methanol synthesis takes place in cartridge 15. Valves 18 and 20 are then closed, and valves 21 and 22 opened so that hydrogen supplied via valve 21 sweeps the synthesised methanol from cartridge 15, via valve 22, to the downstream operations, e.g. methyl iodide synthesis.

Figure 4:
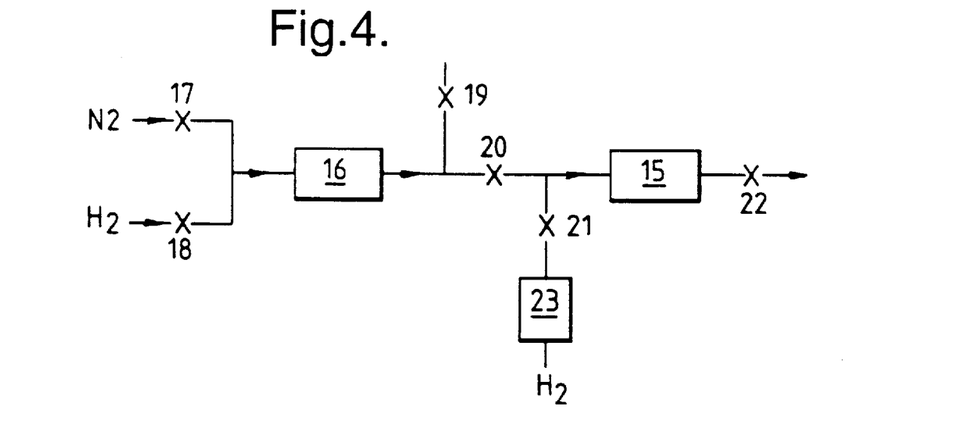

In a variant of the process, shown in FIG. 4 (wherein the reference numerals have the same significance as in FIG. 3) a further cartridge 23 is provided in the line supplying hydrogen to valve 21. This cartridge 23 contains a reagent that upon heating in the presence of hydrogen gives hydrogen iodide. Suitable reagents are easily reducible metal iodides, e.g. silver, copper, mercury, or nickel iodides. Upon completion of the methanol synthesis as described above in relation to FIG. 3, valves 18 and 20 are closed and valves 21 and 22 opened. At the same time cartridge 23 is heated so that a mixture of hydrogen and hydrogen iodide is passed through valve 21 into cartridge 15: the hydrogen iodide displaces the methanol from the catalyst in cartridge 15. In some cases it may be possible to effect reaction of the hydrogen iodide with the methanol in cartridge 15 so that the methanol is converted therein into methyl iodide which is then flushed out of cartridge 15 in the hydrogen stream through valve 13. In this case, it may be desirable to provide a bed of an absorbent for hydrogen iodide at the downstream end of cartridge 15 to prevent hydrogen iodide appearing in the stream emerging from cartridge 15 via valve 13. A suitable absorbent is alkalised alumina.

Figure 5:
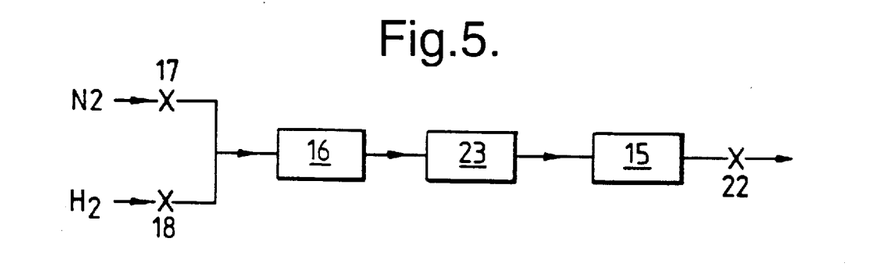

A further variant of this process is described in relation to FIG. 5 wherein valves 19, 20, and 21 are omitted and the cartridge 23 of hydrogen iodide source is interposed between cartridges 16 and 15. In this case, valves 17 and 22 are initially open and valve 18 is closed. Cartridges 16, 23 and 15 are thus purged with nitrogen, typically at about atmospheric pressure, venting through valve 22. Cartridges 16, 23 and 15 are maintained at about ambient temperature. Valves 17 and 22 are then closed. Cartridge 16 is then heated to desorb the carbon oxides from the molecular sieve and valve 18 is opened. Hydrogen is thus supplied to cartridge 15 via valve 18, cartridge 16, and cartridge 23, to pressurise cartridge 15 to, for example, 50 bar abs. and at the same time sweeping the carbon oxides desorbed from cartridge 16 into cartridge 15. The carbon oxides desorbed from cartridge 16 become adsorbed on the methanol synthesis catalyst in cartridge 15. Cartridge 15 is then heated to the desired methanol synthesis temperature and the adsorbed carbon oxides react with the hydrogen to form methanol. Cartridge 23 is then heated to introduce hydrogen iodide into the hydrogen atmosphere. Valve 22 is then opened so that the hydrogen bearing the hydrogen iodide passes into cartridge 15: the hydrogen iodide displaces the methanol from the catalyst in cartridge 15 and reacts to form methyl iodide which passes with the hydrogen through valve 22. As in the embodiment of FIG. 4, it may be desirable to provide a bed of a suitable hydrogen iodide absorbent at the downstream end of cartridge 15.

Figure 6:
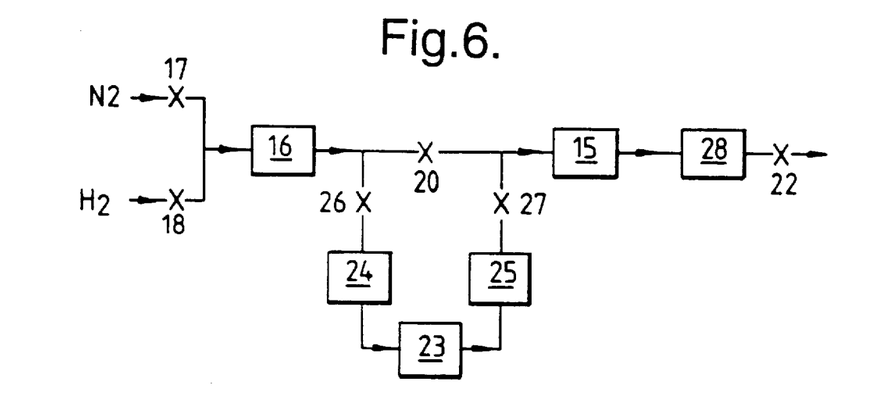

Another variant is shown in relation to FIG. 6. In this embodiment, a valve 20 is provided between molecular sieve 16 and methanol synthesis catalyst 15. A bypass line is also provided. This bypass line has a molecular sieve 24 loaded with water, a hydrogen iodide source 23 such as silver iodide, and a molecular sieve 25 and can be isolated from molecular sieve 16 and methanol synthesis catalyst 15 by means of valves 26 and 27. Downstream of methanol synthesis catalyst 15 is an adsorbent 28 for hydrogen iodide. Molecular sieves 24 and 25 may be in the same vessel as the hydrogen iodide source 23, i.e. as a series of beds within a single vessel. Likewise adsorbent 28 may be a bed downstream of the methanol synthesis catalyst 15, but in the same vessel as catalyst 15. Operation of this arrangement is similar to those described above: after synthesis of methanol in catalyst 15, valve 20 is closed and valves 26 and 27 are opened. Hydrogen passes through the bypass line and molecular sieve 24 is heated to desorb water. Hydrolysis of the silver iodide 23 takes place, producing hydrogen iodide. Unreacted water is adsorbed by molecular sieve 25 and the hydrogen stream containing the hydrogen iodide passes via valve 27 into the methanol synthesis catalyst 15. The methanol on the catalyst is displaced by the hydrogen iodide and reacts to form methyl iodide. The latter is then swept out of the methanol synthesis catalyst via adsorber 28 and valve 22. Unreacted hydrogen iodide is adsorbed in adsorber 28.

In the embodiments described above, the $^{11}C$ carbon oxides were produced by proton bombardment of a nitrogen target in e.g. a cyclotron, and then adsorbed on to a molecular sieve. In some cases it may be possible to omit the molecular sieve adsorption step and utilise the methanol synthesis catalyst as the adsorbent for the carbon oxides: thus the nitrogen from the target is contacted with the methanol synthesis catalyst at e.g. ambient temperature so that the carbon oxides are adsorbed by the catalyst. The vessel, e.g. cartridge, containing the methanol synthesis catalyst is then pressurised with hydrogen and heated to effect the methanol synthesis. If this procedure is adopted, the nitrogen employed as the target should have only a very low oxygen content so that, while some oxygen is available for reaction of the $^{11}C$ produced by the proton bombardment, there is insufficient oxygen to effect any substantial oxidation of the methanol synthesis catalyst.

By the process of the invention, $^{11}C$ produced by proton bombardment of a nitrogen target may be converted into methanol, or derivatives thereof, in a short time so that the product methanol, or methanol derivative, despite the inevitable contamination with $^{12}C$, has a high specific activity, typically of the order of above 4, especially 4 to 10, Ci/$\mu$mol, and in some cases above 20 Ci/$\mu$mol.

As indicated above, it is often desirable to convert the methanol into methyl iodide. In some cases, e.g. where the methanol is displaced from the catalyst using hydrogen iodide, methyl iodide may be formed in situ. However in other instances, the synthesised methanol can be converted to methyl iodide by reaction with a suitable source of iodide.

In accordance with a further aspect of the invention, methyl iodide is synthesised from the methanol by reaction with a suitable solid reagent. Heretofore diphosphorus tetraiodide or an alkali metal iodide, e.g. potassium iodide, on a suitable support, e.g. an aluminosilicate, have been employed; see for example "Int. J. Appl. Radiat. Isot." Vol 36 (1985) p 435–438 and "J. Radioanalytical Chem." Vol 65 (1981) p 61–73. However we have found that high conversions of the methanol to methyl iodide can be obtained by incorporating a suitable acid on to the support together with the iodide. Acids that may be used include those having a non-nucleophilic anion. Examples of suitable acids include o-phosphoric acid, boric acid, sulphuric acid, tungstic acid and niobic acid. Supports that may be used include silica or zeolites, particularly in the hydrogen form, e.g. the hydrogen form of zeolite Y. The iodide is preferably an alkali metal iodide, especially potassium, or cesium, iodide. The reagent may be made by impregnating the support with the iodide and acid in solution in a suitable solvent, particularly water, followed by drying. The acid is preferably present in a substantial molar excess compared to the iodide: preferably there are 5 to 25 gram moles of acid per gram atom of iodine. The iodide is preferably present in such an amount that there are 0.0025 to 0.01 gram atoms of iodine per 100 g of support.

The carrier gas is preferably that employed for the methanol synthesis so that the product from the methanol synthesis can be fed directly to the methyl iodide synthesis step. The methyl iodide synthesis is effected at elevated temperatures, preferably between 100° and 200° C., particularly 130°–190° C. The pressure may be any convenient pressure from atmospheric up to the pressure used in the methanol synthesis step. As in the case of the methanol synthesis step, the methyl iodide synthesis may be effected in continuous flow or in batch flow. In the latter case, where the methanol is effected in batch flow conditions, the carbon oxides can be desorbed by heating the molecular sieve under an atmosphere of carrier gas (which may as described above be, or contain, hydrogen at elevated pressure, then establishing communication between the vessel containing the carrier gas containing the desorbed carbon oxides and the vessel containing the methanol synthesis catalyst, then after a suitable period, e.g. 1–2 minutes, has elapsed to allow synthesis of methanol to occur, connection is established between the vessel containing the methanol synthesis gas and the vessel containing the reagent for the synthesis of methyl iodide.

It is generally desirable to remove water and any hydrogen iodide from the carrier gas after passage over the methyl iodide synthesis reagent. This may be effected by passing the carrier gas, containing the synthesised methyl iodide through a suitable absorbent, e.g. a molecular sieve or alkalised alumina. This absorbent may be disposed in the same vessel as the methyl iodide synthesis reagent.

As in the case of methanol synthesis, the reagent used for the methyl iodide synthesis may be disposed in a cartridge. The cartridge may be similar to that employed for the methanol synthesis step, i.e. similar to that shown in FIG. 1. Where an absorbent is employed this may be disposed in the same cartridge as a bed downstream of the methyl iodide synthesis reagent. The volume of reagent required is generally less than 1 ml, e.g. 0.3 to 0.8 ml, and where an absorbent is employed, this may also have a volume of less than 1 ml.

If the syntheses of methanol and methyl iodide are effected under the same conditions of temperature and pressure, a single cartridge may be employed with the methanol synthesis catalyst disposed as a bed upstream of the bed of methyl iodide synthesis reagent. However to avoid the risk of poisoning the methanol synthesis catalyst with iodide from the methyl iodide synthesis reagent, a guard bed of a suitable guard material is preferably disposed between the methanol synthesis bed and the methyl iodide synthesis reagent.

Before use, the vessel, e.g. cartridge, containing the methyl iodide synthesis reagent should be purged with a stream of an inert gas to minimise the carbon oxides content, and then sealed.

The synthesised methyl iodide can be recovered from the carrier gas by trapping in a suitable solvent, e.g. tetrahydrofuran or acetone, and converted into the desired tracer compound by known techniques.

The invention is illustrated by the following Examples.

EXAMPLE 1

This example demonstrates the need for pre-conditioning a nickel catalyst when employed for the production of methane from carbon dioxide.

A stream of a carbon dioxide/hydrogen mixture (1 vol $CO_2$:10 vol $H_2$) was passed at a pressure of 5 bar abs. and at 200° C. over a freshly reduced commercial supported nickel methanation catalyst. For the first 5 minutes after commencing the flow of the carbon dioxide/hydrogen stream, no methane was detected in the effluent gas, and thereafter the yield of methane gradually increased. The time to achieve the steady state maximum yield was 40 min. This is shown in the following table.

| Time (min) | Methane yield (as % of steady state yield) |
| --- | --- |
| 10 | 15 |
| 25 | 39 |
| 30 | 51 |
| 35 | 58 |
| 40 | 100 |

The stream of carbon dioxide and hydrogen was then stopped and the process shut-down, maintaining the catalyst in the reduced state. On recommencing the process, the steady state yield of methane was attained immediately upon commencing the flow of the carbon dioxide/hydrogen stream.

EXAMPLE 2

In this example, the conversion of methanol to formaldehyde was studied over a silver catalyst. A stream of methanol in nitrogen as a carrier was passed at atmospheric pressure and at 355° C. over a fresh silver catalyst. Although immediately there was a high conversion of methanol, about 98%, i.e. very little methanol was observed in the effluent gas, the yield of formaldehyde was initially low and only increased gradually to a steady state as shown in the following table.

| Time (min) | Formaldehyde yield (% of steady state yield) |
|---|---|
| 15 | 21 |
| 45 | 36 |
| 75 | 100 |

After running for a total of less than 4 hours, the process was shut down by replacing the methanol/nitrogen stream with a stream of nitrogen and cooling catalyst to room temperature. The reactor was then sealed and left for 64 hours. After this period the reaction was reconnected to a nitrogen stream and heated to 355° C. whereupon the flow of the methanol/nitrogen stream was recommenced, giving immediately a yield of formaldehyde equal to the steady state yield prior to shut-down.

EXAMPLE 3

The conversion of carbon dioxide to carbon monoxide can be performed catalytically by the reverse water gas shift reaction. This example illustrates that there is a delay associated with the use of a catalyst that has not been pre-conditioned.

A fresh copper-containing catalyst (0.1 g) was reduced with hydrogen and then a stream of hydrogen was passed over the catalyst at atmospheric pressure and at 220° C. At intervals 4 µmol pulses of carbon dioxide were introduced into the stream of hydrogen. With successive pulses, the conversion of the carbon dioxide in the pulse increased, until after 6 pulses a steady state condition was reached where was no increase in the carbon dioxide conversion. The carbon dioxide conversion (as a percentage of the steady state conversion) for the first 6 pulses ius shown in the following table.

| Pulse | $CO_2$ conversion (as % of steady state conversion) |
|---|---|
| 1 | 0 |
| 2 | 28 |
| 3 | 44 |
| 4 | 60 |
| 5 | 88 |
| 6 | 100 |

EXAMPLE 4

A stream of carbon monoxide (1 vol) and chlorine (12.5 vol) was passed over a commercial activated carbon catalyst (0.15 g) at a pressure of 5 bar abs. at 250° C. Initially there was no production of phosgene ($COCl_2$). Slowly the production of phosgene increased until steady state was achieved as shown in the following table.

| Time (min) | Phosgene yield (as % of steady state yield) |
|---|---|
| 10 | 0 |
| 13 | 1 |
| 16 | 20 |
| 19 | 63 |
| 28 | 100 |

At this point the catalyst was fully conditioned. The reaction was then shut down and the catalyst flushed with an inert gas. On recommencing the reaction, no delay was observed in the production of phosgene and the yield was the same as that for the fully conditioned catalyst prior to shut down.

EXAMPLE 5

A freshly reduced supported copper catalyst (0.1 g) was pre-conditioned for methanol synthesis by treating it with a stream of a gas mixture containing carbon monoxide (1 vol)/carbon dioxide (1 vol)/hydrogen (8 vol) at 20 bar abs. at 220° C. for 2 hours. The reactor was then sealed under inert gas and taken to a cyclotron facility where it was connected into apparatus having the general layout shown in FIG. 3

$^{11}CO_2$ was produced in the cyclotron facility in a nitrogen carrier and trapped in a molecular sieve. The carrier gas was then changed to hydrogen and the system pressurised to 50 bar abs. The hydrogen stream passed through both the molecular sieve and the methanol catalyst cartridge. The catalyst was heated to 200° C. and then the molecular sieve was heated to release the $^{11}CO_2$ into the hydrogen stream so that it passed into the catalyst cartridge and contacted the catalyst.

The effluent gas from the catalyst cartridge was analysed by radio-HPLC. No product other than methanol was detected The amount of $^{11}CH_3OH$ obtained was 57 mole % of the $^{11}CO_2$ produced by the bombardment The above procedure was repeated but using apparatus as shown in FIG. 6. After contact of the $^{11}CO_2$-containing hydrogen stream with the catalyst, a pulse of hydrogen iodide was introduced via a hydrogen iodide dosing system. The hydrogen iodide desorbed the methanol from the catalyst and reacted therewith to form methyl iodide which was trapped in ethanol. HPLC analysis of the solution revealed that the only product was methyl iodide: no other products were detected by HPLC, or radiochemical analysis. The estimated of the specific activity of the $^{11}CH_3I$ was 10 Ci/µmole.

As described above, methanol can be desorbed from the catalyst and converted to methyl iodide by introducing hydrogen iodide. Where methanol, rather than methyl iodide, is required as the product, an alternative desorbing agent may be employed as shown in the following example.

EXAMPLE 6

A freshly reduced copper-containing catalyst was pre-conditioned by operation for methanol synthesis for 2.5 hours at 50 bar abs. and at 200° C. using a gas mixture containing carbon monoxide (1 vol)/carbon dioxide (1 vol) /hydrogen (8 vol). The gas stream was then replaced by a hydrogen gas stream. Methanol was produced by pulsing a small aliquot of carbon dioxide (approx 1 µmol) into the hydrogen carrier and passing the mixture at 50 bar abs. over the catalyst which was maintained at 200° C. No methanol or carbon dioxide was detected in the effluent gas stream after each pulse. The catalyst was then cooled to room temperature and a pulse of hydrogen sulphide (approx. 0.1 mmol) was introduced into the gas stream and passed over the catalyst. No hydrogen sulphide was detected in the effluent gas, but an equilibrium mixture of carbon monoxide, carbon dioxide and methanol was detected. In this equilibrium mixture, 95% of the carbon is in the form of methanol.

We claim:

1. A catalytic process for the reaction of a carbon-containing compound as a primary reagent comprising contacting a carrier gas containing an amount of not more than about 24 μmoles of the primary reagent, together with such other reagent or reagents as may be needed for the reaction, with a catalyst for the desired reaction under reaction conditions favourable to said reaction, wherein the catalyst has been pre-conditioned by previous use for the desired reaction and has been passivated, or has been maintained in the pre-conditioned state, until contacted with said carrier gas, characterised in that the product of the catalytic reaction of the primary reagent is adsorbed on the catalyst and, after effecting said catalytic reaction, said product is desorbed from the catalyst by contacting said catalyst with a stream of a carrier gas containing a compound that is not a carbon compound and which is adsorbed by the catalyst more strongly than said product.

2. A process according to claim 1 for the production of a radio-labelled product wherein the primary reagent is a radio-labelled compound, alone or in admixture with the corresponding unlabelled compound, wherein the pre-conditioning is effected using the unlabelled compound for the pre-conditioning reaction.

3. A process according to claim 1 wherein the desorption is effected by contacting the catalyst with a compound that acts as a poison for the catalytic reaction.

4. A process according to claim 1 wherein the desorption is effected by contacting the catalyst with a compound that reacts with the adsorbed product of the catalytic reaction to give a desorbed desired product.

5. A process according to claim 1 wherein the primary reagent is introduced into the carrier gas stream as one or more pulses.

6. A process according to claim 1 wherein, prior to effecting the catalytic reaction, the primary reagent is adsorbed on to a molecular sieve and is desorbed into the carrier gas stream by heating said molecular sieve.

7. A process according to claim 1 wherein the primary reagent comprises at least one carbon oxide.

8. A process according to claim 7 wherein the primary reagent comprises $^{11}C$ oxides.

9. A process according to claim 7 wherein the primary reagent is introduced as one or more pulses into a hydrogen-containing carrier gas stream and methanol is formed therefrom by passing said carrier gas stream containing said primary reagent, under conditions favourable for the formation of methanol, over a copper-containing catalyst that has been pre-conditioned by use for methanol synthesis.

10. A process according to claim 9 wherein the methanol formed from the primary reagent is adsorbod onto the catalyst and the catalyst is then contacted with a carrier gas stream containing hydrogen iodide, whereby the methanol is converted to methyl iodine which is desorbed into said carrier gas stream.

11. A process according to claim 9 wherein the methanol is converted to methyl iodide by desorbing the methanol from the catalyst into a carrier gas stream which is then passed at an elevated temperature over a solid reagent comprising a support carrying an acid and an iodide selected from alkali metal iodides and diphosphorus tetra-iodide.

\* \* \* \* \*